US006291232B1

United States Patent
Miller, III

(10) Patent No.: US 6,291,232 B1
(45) Date of Patent: Sep. 18, 2001

(54) ANAEROBIC DIGESTION SYSTEM AND PROCESS

(76) Inventor: Herman P. Miller, III, P.O. Box 1769, Stockton, CA (US) 95201-1769

( * ) Notice: Subject to any disclaimer, the term of this patent is extended or adjusted under 35 U.S.C. 154(b) by 0 days.

(21) Appl. No.: 09/414,908

(22) Filed: Oct. 8, 1999

Related U.S. Application Data
(60) Provisional application No. 60/133,720, filed on May 12, 1999.

(51) Int. Cl.[7] ........................................... C07C 1/00
(52) U.S. Cl. .................. 435/262; 435/289.1; 95/139; 95/229; 95/235; 95/236; 96/181; 96/203; 210/605
(58) Field of Search .................. 435/262, 289.1; 95/139, 229, 235, 236; 96/181, 203; 210/603, 605

(56) References Cited

U.S. PATENT DOCUMENTS

| | | | |
|---|---|---|---|
| 3,533,732 | 10/1970 | Moore et al. ........................... | 95/161 |
| 3,981,800 | 9/1976 | Ort ........................................... | 210/6 |
| 4,496,371 | * 1/1985 | Urban et al. ........................ | 48/197 R |
| 4,566,278 | 1/1986 | Force ..................................... | 60/618 |
| 4,599,167 | * 7/1986 | Benjes et al. ........................ | 210/150 |
| 4,957,715 | * 9/1990 | Grover et al. ........................ | 423/228 |
| 5,681,360 | * 10/1997 | Siwajek et al. ..................... | 48/127.3 |
| 6,071,326 | * 6/2000 | Hall ......................................... | 95/41 |

OTHER PUBLICATIONS

Graef et al. "Stability and Control of Anaerobic Digestion", Journal WPCF, vol. 46, No, 4, pp. 666–683, Apr. 1974.
Smart et al. "Full Scale Studies on the Thermophilic Anaerobic Digestion Process", Minister of Supply and Services Canada, Cat. No. En43–11/59, 1977.

Rimkus et al. "Full–Scale Thermophilic Digestion at the West–Southwest Sewage Treatment Works, Chicago, IL" Journal WPCF, vol. 54, pp. 1447–1457. Nov. 1982.

"Sludge Pretreatment Yields Class A Biosolids", Water-World, vol. 11, Issue 6, p. 20, 1/3p, 1c, Sep., 1995.

Praxair Technology, Inc., "Carbon Dioxide for Water Treatment", Web Site http://www.praxair.com, Copyright 1997–1999.

Alatiqi et al., "Kinetic Analysis of Thermophilic Anaerobic Digestion of Wastewater Sludge", Water, Air and Soil Pollution, vol. 107, pp. 393–407, 1998.

Roberts et al. "A Thermophilic/Mesophilic Dual Digestion System for Treating Waste Activated Sludge" Journal of Chemical Technology and Biotechnology 74:445–450 1999.

* cited by examiner

Primary Examiner—David A. Redding

(57) ABSTRACT

Anaerobic digestion system and process in which the raw digester gas containing methane and other gaseous components is cooled at atmospheric pressure in the presence of a liquid to a temperature at which the other gaseous components have a substantially higher solubility in the liquid than methane and are substantially all absorbed into the liquid, leaving pure, dry methane gas. That methane gas is then used in other parts of the system, including the digester and a refrigeration system for cooling the raw gas.

14 Claims, 4 Drawing Sheets

ANAEROBIC DIGESTION SYSTEM AND PROCESS

This application is based on Provisional Application No. 60/133,720, filed May 12, 1999.

This invention pertains generally to anaerobic digesters and, more particularly, to a system and process for improving the efficiency and stability of an anaerobic digester by extracting pure, dry methane gas from the raw gas generated by the digester and using that methane gas in the digester.

Methane gas, a major component of the raw gas by-product of the anaerobic digestion of wastewater sludge, has long been recognized as an important potential energy source. With mesophilic digestion, there is approximately one cubic foot of raw digester gas per day from every man, woman and child contributing to the waste stream. Recently, treatment plants have utilized this raw gas to fire boilers and/or power gas-engine driven electrical generators.

Raw gas generated by digesters will vary a few percentage points in its constituent amounts. A normal sample might typically consist of 61% methane ($CH_4$), 33% carbon dioxide ($CO_2$), 5% water vapor ($H_2O$), and 1% hydrogen sulfide ($H_2S$) Pure methane has a heat value of 1000 BTU/$ft^3$ of gas at standard conditions of temperature and pressure, and raw gas has a heating value of about 600 BTU/$ft^3$.

Anaerobic digesters usually operate in the mesophilic temperature range of 30° C. to 38° C., with a set point of 35° C. There are also a few digesters that operate in the psychrophilic temperature range of 10° C. to 20° C. and the thermophilic temperature range of 49° C. to 57° C. The system and process described herein are applicable to all three ranges, although specific reference is made only to mesophilic digester operation at 35° C. and thermophilic digester operation at 55° C.

A digester operated in the mesophilic or thermophilic range must not only hold its temperature close to 35° C. or 55° C., but must also hold its pH in the range of 6.6 to 7.6. Pressure is usually held in the range of 4 to 10 inches above atmospheric pressure for gas flow control purposes, and the elevated temperature is responsible for a substantial part of the operational cost in a digester system. Hot water boilers, often fueled by raw gas from the digester, are commonly used to maintain this temperature control. In colder climates, special insulation is required, and burning raw gas for digester heat is inefficient and corrosive to boiler tubes. Using raw gas to power gas or gas/diesel engines for pumping or generating electrical power is undesirable from the standpoints of corrosiveness and volumetric inefficiency. The system and process of the invention not only remove all the unwanted components of the raw gas, but in addition heat the return gas used in mixing, thus significantly decreasing the requirement for additional digester heat.

Typically, the raw gas generated in wastewater, solid waste and/or landfill processes is recycled in order to provide mixing of the liquor in the digestion process. The use of raw gas in mixing is an aid to bacterial growths that break down the bio-solids in the anaerobic digestion process. Raw gas is recycled in the digestion process by various methods. The invention applies to all gas mixing methods.

Anaerobic digestion is a two-stage process which may take place in a single vessel, in which case it is sometimes referred to as single stage digestion. It may also take place in two separate vessels, in which case it is commonly referred to as two stage digestion. It is the combined action of two forms of bacteria that live together in the same environment and are commonly referred to as the "acid formers" and "methane fermenters" It is necessary to keep a balance between these two bacteria. Acid formers are abundant in raw sewage. Methane fermenters are not nearly so prevalent and require a pH of 6.6 to 7.6 to produce. A digester is sensitive to too much food, it may easily become too acidic, or "go sour", and fail to produce the desired innocuous dewaterable sludge and valuable methane ($CH_4$). The system and process of the invention remove the acidic component from the mixing gas, increase the volumetric gas flow, and stabilize the system over a much broader range of feed conditions by removing the acids and acid forming products from the mixing gas.

The carbon dioxide in the raw gas forms carbonic acid ($H_2CO_3$) which, when returned to the digester as a component of the mixing gas, moves the balance in the direction of the already predominant acid formers and destroys the volumetric efficiency of any gas-to-energy processes to which it may be applied. The water vapor condenses in lines, equipment, and instrumentation used to monitor and control gas flow. However, the methane component is a valuable component, both as a gas that may be drawn from the system for energy and as a mixing gas. It is also believed that the presence of methane is a further aid to the health of methane fermenters. Natural gas, which contains a high percentage of methane, is sometimes used to restart sour digesters.

Several methods of separating (scrubbing) methane from the other raw gas constituents have been developed. U.S. Pat. No. 3,981,800, for example, describes a system in which the gas in a digester is pressurized to a level of 2 to 5 atmospheres (approximately 30 to 75 psig) so that the digesting organic waste preferentially absorbs carbon dioxide. The application of these processes to wastewater treatment plants has not proven practical and/or economically feasible. The present invention provides clean methane gas that is dry, cold and dense at atmospheric pressure, and it also overcomes the limitations and disadvantages of other processes and enhances the operational efficiency of the plant.

The thermophilic digestion process has never been considered to be an economically viable solution to the treatment of sludge in a full sized digester with a capacity of some 300 to 500 thousand gallons. Prior to this invention, there has never been an economical heat source capable of maintaining the additional 20° C. required for thermophilic operation. Thermophilic digestion is about three times as fast as mesophilic digestion. For example, a thermophilic digester can reduce the same amount of volatile solids in 10 days that a mesophilic digester will reduce in 32 days. Consequently, a thermophilic digester produces about three times as much methane gas in a given time period. By providing the heat required to raise and maintain the operating temperature in the thermophilic range, the basic digester operating efficiency has increased by a factor of three.

Utilization of the methane energy component of this raw gas has been hampered by the presence of the other by-product components. The most harmful by-product with respect to repair, maintenance and replacement of equipment in the mixing and/or gas to energy systems (iLe., pumps, blowers, compressors, boiler tubes, cylinders, etc.) is the condensing water vapor and the dilute sulfuric acid ($H_2SO_4$) produced by the hydrogen sulfide and water in the raw gas. In addition, the volumetric inefficiency of using a gas that is 40% inert in gas-engines used for pumping or generating systems requires much larger and more expensive engines than the service requirement would otherwise dictate, accompanied by a corresponding reduction in operating efficiency. Additionally, passing carbon dioxide through the combustion process increases the "greenhouse" effect upon the atmosphere.

Because of the unreliability, high maintenance costs, and the low time between failures, many plants have abandoned the use of raw gas altogether in favor of natural gas (domestic or pipeline), opting to flare-off the raw digester gas and its harmful components to the atmosphere.

Secondary sludge (sludge from the secondary sedimentation basins and the aerobic treatment processes) tends to be thinner than primary sludge sludge from the primary sedimentation basins). In order to handle secondary sludge effectively, whether it is used in direct land application or cycled through the digester, it is customary to thicken this sludge. This requires rather elaborate and expensive equipment with chemicals such as polymers to aid the process. By cycling all the sludge through the digester, which is dewatered continuously in the invention, the requirement for a separate sludge thickening process is eliminated. Thickening of the sludge in the digester takes place automatically and continually as the water is removed from the recalculating gas.

The U.S. Environmental Protection Agency has recently mandated that sludge must be pasteurized to below harmful pathogens levels for unrestricted use or access land application, Subjecting sludge to thermophilic temperatures for as little as one hour provides this pasteurization. Systems of this type have been in use in Europe for a number of years and are becoming more common in the United States. The equipment involved in such a process is expensive and adds complexity to the treatment process. The invention subjects all sludge to pasteurization, thereby eliminating the need for a separate process while providing a positive environmental impact.

Typically the effluents of wastewater treatment plants tend to run alkaline (i.e., to have a pH in excess of 7.0). In a large number of plants with certain types of industrial influent the pH range becomes excessively caustic, failing discharge requirements and impeding disinfection. Equipment is being installed in wastewater treatment plants today solely for the injection of bottled $CO_2$ gas into the effluent prior to chlorination or other disinfect ion process. Carbon dioxide provides superior process control by virtue of its self-buffering characteristics. It is being used to replace older systems that use hydrochloric acid, sulfuric acid or acetic acid. The invention eliminates the need for either of these systems. The carbon dioxide and hydrogen sulfide removed from the raw digester gas is dissolved in water which is inserted into the secondary effluent stream. In addition, maintaining this buffer reduces the amount of chlorine required for disinfection and eliminates the discharge of carbon dioxide to the atmosphere.

Nearly all wastewater treatment processes work better and faster with heat. This is true in the aerobic process as well as in the anaerobic process. With the invention, the amount of heat available to the process is a direct function of the cooling required, which is in turn is a direct function of the volumetric rating of the gas compressor. Varying amounts of excess heat will become available, depending upon the requirements of the basic components, their process variables, ambient temperature, insulation, etc. All excess heat is utilized in preheating the digester sludge and/or increasing the temperature and efficiency of the aerobic process.

It is in general an object of the invention to provide a new and improved anaerobic digestion system and process.

Another object of the invention is to provide a system and process of the above character which produces pure, dry methane gas from the raw anaerobic digester gas.

Another object of the invention is to provide a system and process of the above character which stabilizes the anaerobic digestive process and simplifies the wastewater treatment process.

These and other objects are achieved in accordance with the invention by providing an anaerobic digestion system and process in which the raw digester gas containing methane and other gaseous components is cooled at atmospheric pressure in the presence of a liquid to a temperature at which the other gaseous components have a substantially higher solubility in the liquid than methane and are substantially all absorbed into the liquid, leaving pure, dry methane gas. That methane gas is then used in other parts of the system, including the digester and a refrigeration system for cooling the raw gas.

Figure 1:
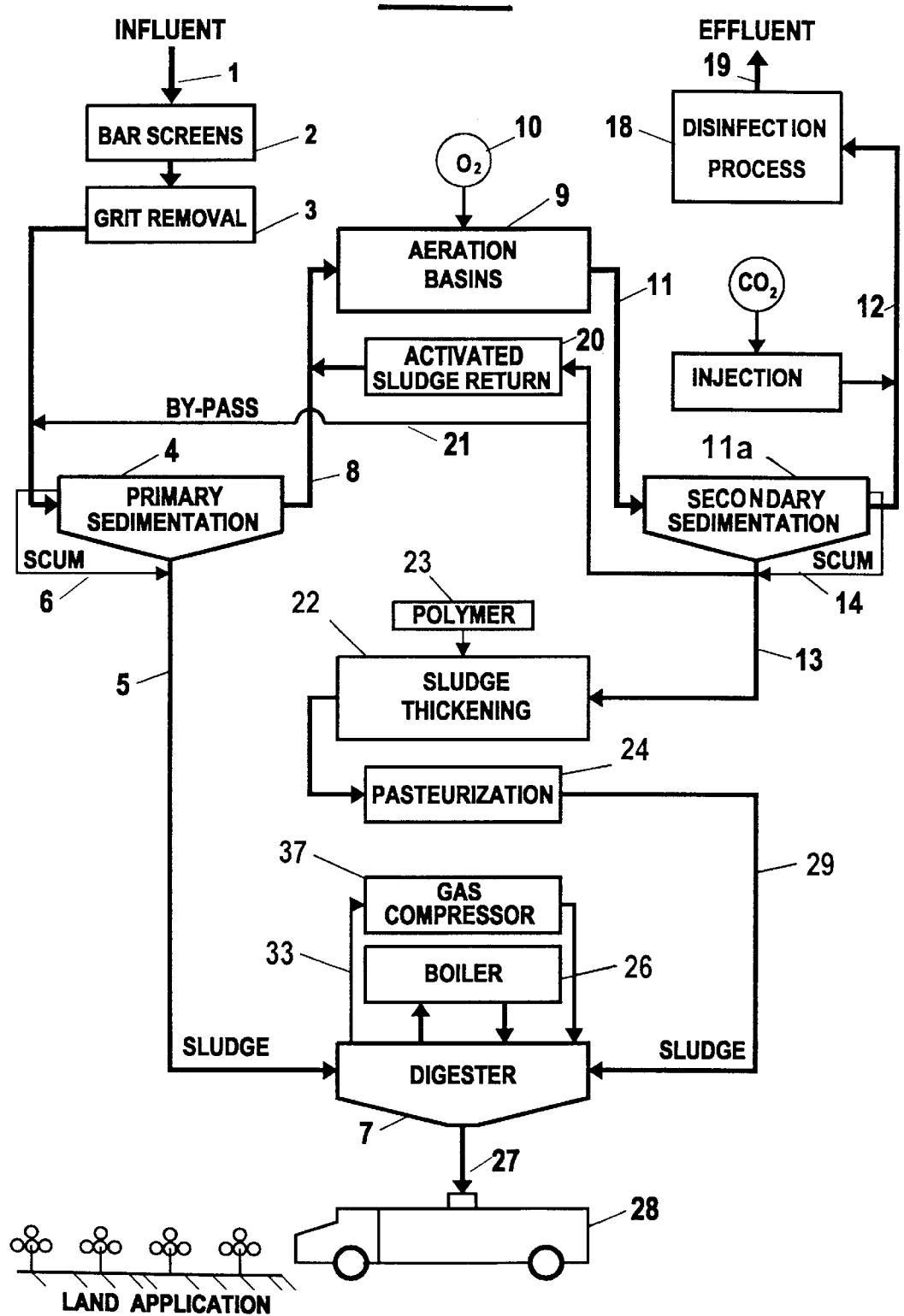
FIG. 1 is a schematic diagram of a typical municipal wastewater treatment plant of the prior art.

In a typical wastewater treatment plant (FIG. 1), an influent 1 passes through a bar screen 2 and grit remover 3 where rags, rocks, wood, condoms, plastics, sand, etc. are removed for burial. The influent is then introduced into a primary sedimentation tank 4 where undissolved materials are allowed to settle to the bottom as primary sludge or to rise to the top as scum. The scum is added to sludge and pumped through lines 5 and 6 to a digester 7, and the primary effluent passes through line 8 to one or more aeration basins 9. There, some form of oxygen 10 is injected into or mixed with the effluent to promote the growth of aerobic bacteria. These bacteria ingest and biodegrade the effluent to produce a liquor which passes through line 11 to a secondary sedimentation tank 11a. The output of this tank consists of clear secondary effluent, sludge and scum. A buffering solution is added to, or injected into, the secondary effluent by a carbon dioxide tank 16 and an injection pump 17. This effluent then passes line 12 to a final disinfection processor 18, then to a discharge line A certain percentage of the secondary activated sludge is pumped back to aeration basins 9 through a line 30 and a pump 20 to further promote the bacterial growth, or is bypassed to the primary sedimentation tank 4 through a line 21. The secondary sludge and scum are routed through lines 13, 14 to a sludge thickener 22 where a polymer 23 is added. The polymer promotes coagulation and the formation of a sludge cake of four to seven percent solids that is passed through pasteurizer 24 before passing through line 29 to an anaerobic (mesophilic) digester 7. In the digester, the sludge is mixed and agitated by cycling the raw digester gas that forms above the liquor through a compressor 37. A boiler 26 keeps digestion temperature at a level of about 35° C., and the sludge is retained in the digester for a mean time of 20 days before being discharged through outlet 27 to a truck 28 for use as a fertilizer.

It should be noted that maximum production of raw gas in a mesophilic system occurs with a mean retention time of 32 days. Most wastewater treatment plants do not have the capacity for this retention time, and most plants seem to operate in the range of 20 to 25 days of mean digester retention. Ideally, the digester would be operated as a continuous flow process. However, for practical purposes step feed and simultaneous step discharge are commonly used. In anaerobic digestion, as the name implies, the tank is a closed container with either a floating roof or a solid roof, and room at the top for gas collection. No oxygen is allowed to enter the portion of the tank where the gas is collected.

The influent process flow 1 varies from plant to plant from a few thousand gallons per day to about one hundred million gallons per day, with the most common flow rates are in the range of 2 to 20 million gallons per day. Processes are adapted to treat wastewater from any source and/or combination of sources having organic and/or other contaminants suitable for being acted upon by microorganisms to reduce the amount of contamination, especially elements creating an oxygen demand therein. The influent may come from a wide variety of sources not limited to municipal human wastewater, including breweries and distilleries; chemical plants; ethanol plants; dairy and cheese plants; fruit and vegetable canaries; food processing plants; grain processing plants; meat, fish, and poultry plants; pulp and paper plants; and sugar factories. The process may also digest added biological waste such as animal manure, agricultural wastes, and soluble solid wastes such as those containing cellulose wastes (e.g., paper, cardboard, etc.) that are added to the waste stream in slurry form.

Figure 2:
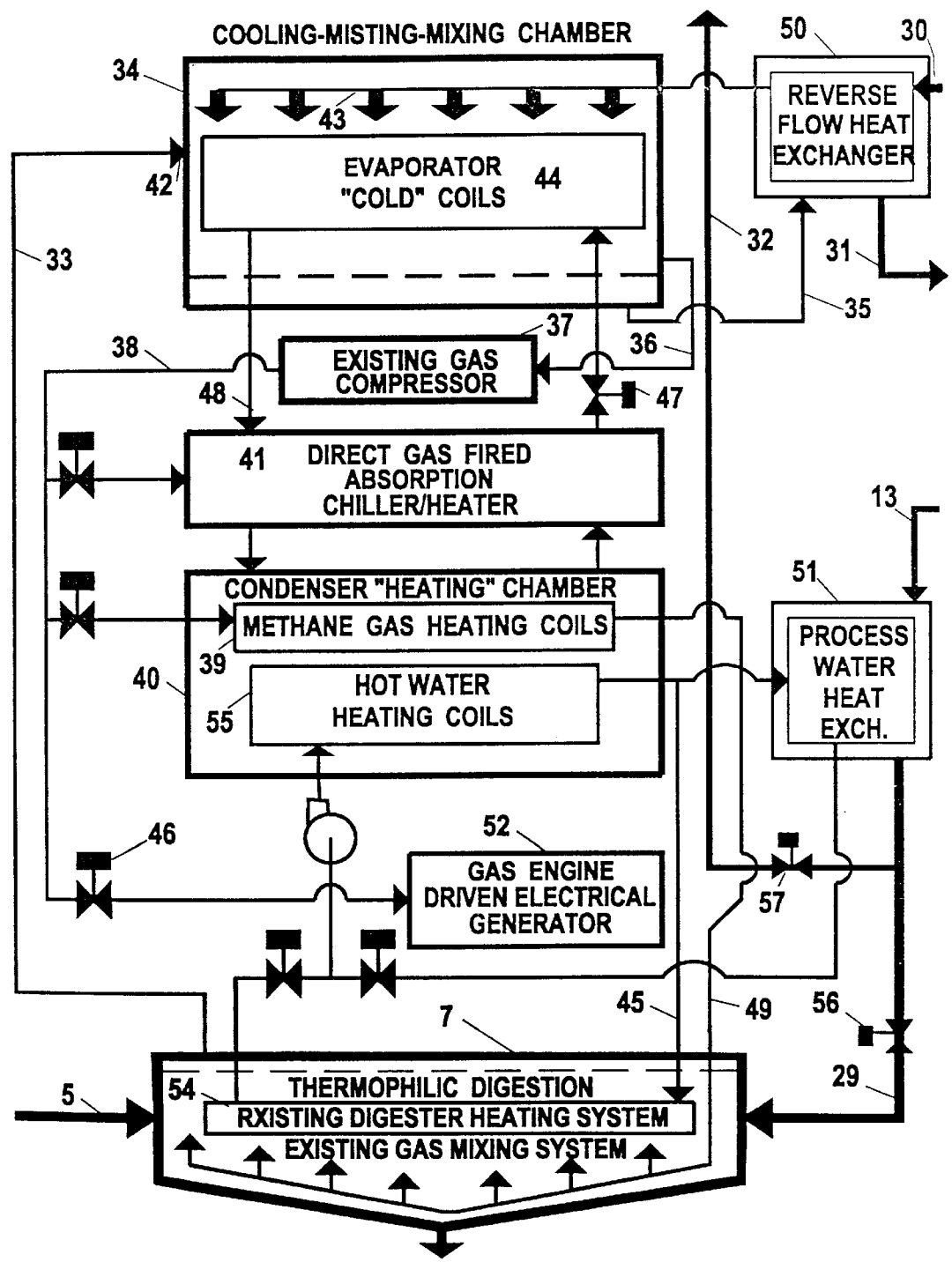
FIG. 2 is a schematic diagram of one embodiment of an anaerobic digestion system incorporating the invention.
Figure 3:
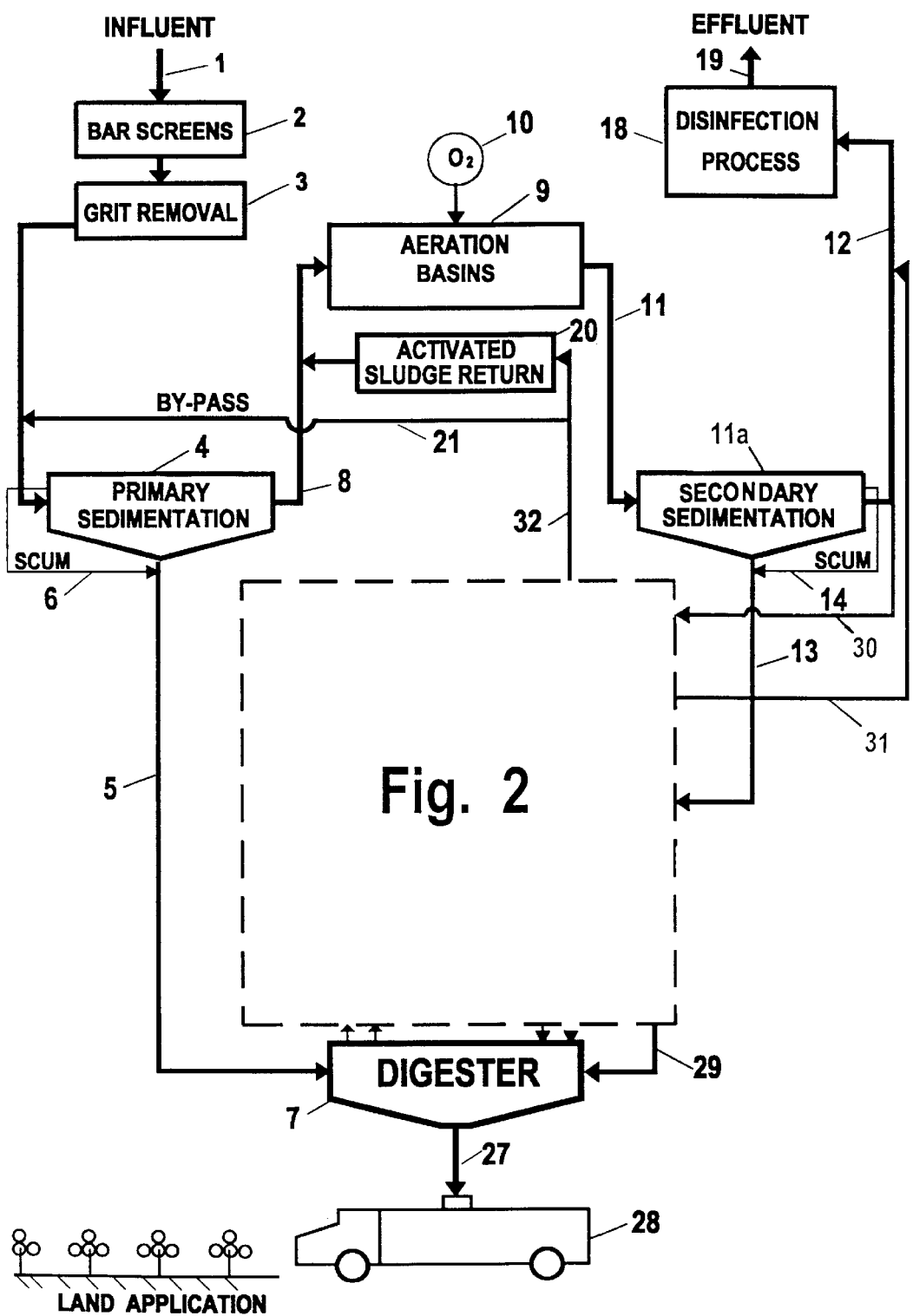
FIGS. 3 and 4 are schematic diagrams illustrating the incorporation of the embodiment of FIG. 2 into the wastewater treatment plant of FIG. 1.
Figure 4:
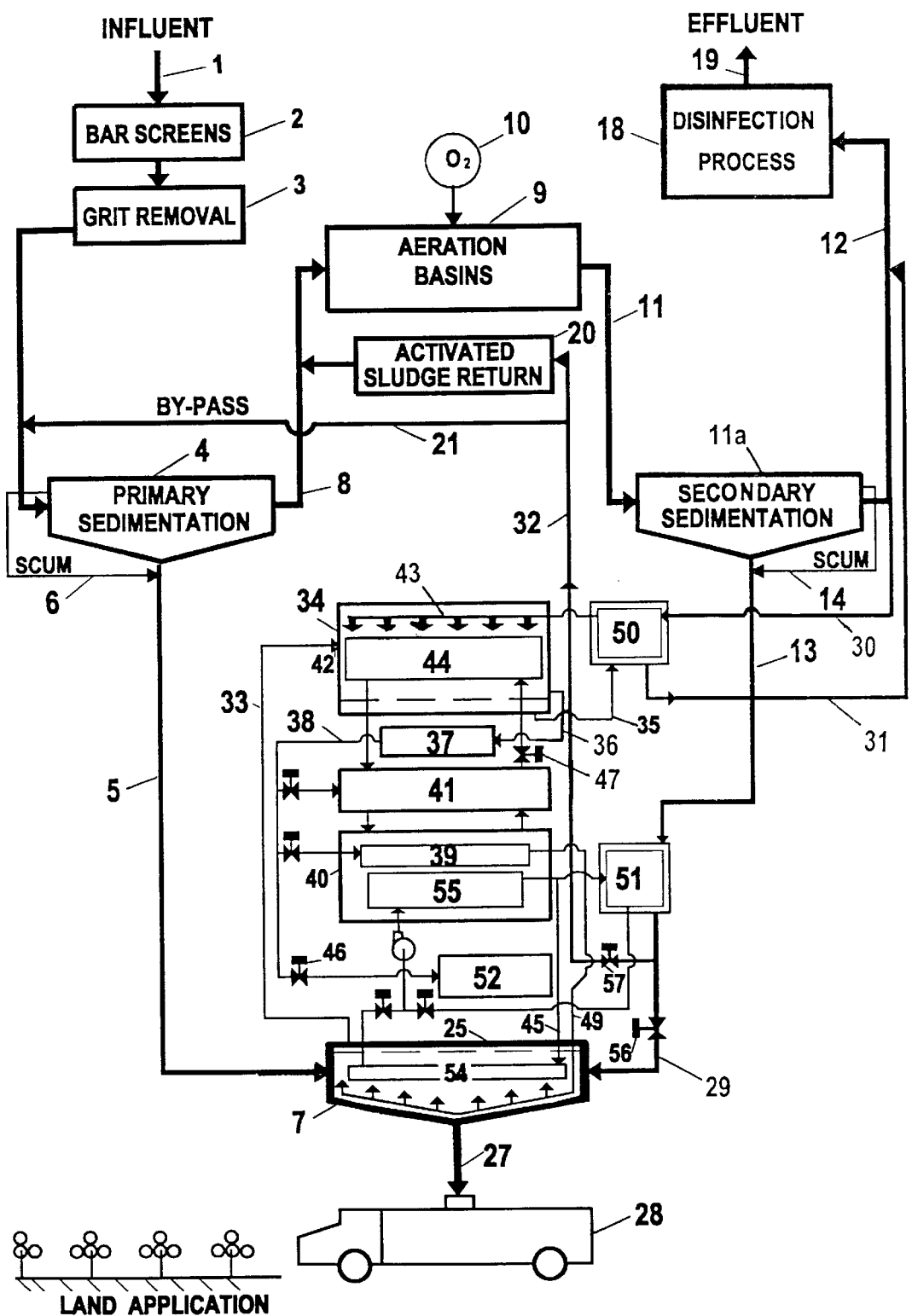

As illustrated in FIGS. 2–4, the raw gas from digester 7 is introduced into a misting chamber 34 where its temperature is reduced from about 35° C. or 55° C. to about 2° C.–5° C. In the misting chamber, the gas is progressively mixed with finely misted cool process water from secondary sedimentation tank 11a and cooled by evaporator coils 44 until its constituent gases are either absorbed into solution or exit from the chamber as gas. The process water is taken from the wastewater treatment system effluent line 12 just prior to the final disinfection. This water is commonly referred to as "No. 4 water". The misting chamber operates at atmospheric pressure, and the temperature is thermostatically controlled.

At the temperature and pressure at which the misting chamber are operated, the carbon dioxide, water vapor and hydrogen sulfide components of the raw waste gas have a substantially greater solubility in water than methane gas does. This relationship is illustrated in the following table:

Table of Solubility of Digester Gases

| TEMPERATURE | SOLUBILITY (Milliliters per liter of $H_2O$) | | |
|---|---|---|---|
| ° C. | $CH_4$ | $CO_2$ | $H_2S$ |
| 35 | 22 | 480 | 500 |
| 30 | 23 | 540 | 1650 |
| 25 | 25 | 610 | 1850 |
| 20 | 28 | 700 | 2000 |
| 15 | 31 | 820 | 2300 |
| 10 | 36 | 1000 | 2600 |
| 5 | 43 | 1200 | 2850 |

Because of these differences in solubility, the carbon dioxide, water vapor and hydrogen sulfide are almost totally absorbed into the water, leaving pure, dry methane gas.

The misting water flow rate is adjusted to insure complete solution of carbon dioxide, but is minimized to conserve energy. The cold, dry, dense methane gas from the misting chamber is delivered through line 36 to the existing gas pump, blower, or compressor 37 for the gas mixing system. Having been stripped of its sulfides, the cool, dry methane increases the efficiency of the pumping system and reduces the maintenance requirements of the equipment.

With a raw gas containing approximately 61% methane, 33% carbon dioxide, 5% water vapor and 1% hydrogen sulfide, the removal of the water vapor and gases other than methane reduces the volume of the scrubbed gas by approximately 40% of the raw gas volume. However, the gas compressor 37 will operate as before, but with additional volumetric efficiency of 20%, or more, since it is now working with a cold gas. Consequently, there is more demand for raw gas, and the amount of raw gas processed by the mixing system is increased by an overall factor of about 2. To avoid starving the mixing compressor 37, the diameter of the piping 33 between the digester 7 and the misting chamber 34 may need to be increased. Care must also be taken to maintain a virtually closed system.

Having been cleansed of the acid products of the raw gas and being at a lower temperature than normal, the cold dry methane gas fed to mixing compressor 37 is not only pumped more efficiently but is also significantly more useful in the digestive process. The compressor increases the pressure of the gas to about 5–20 psig, and feeds the gas through line 38 to the heating coils 39 of a condenser heating chamber 40. There, the heat previously removed from the raw gas in misting chamber 34 is added back to the methane, raising the temperature of the gas to a range somewhat above 35° C. or 55° C. This increases the volumetric mixing effectiveness of the gas by about 200%, or more.

The hot dry methane gas from heating chamber 40 passes through line 49 to the existing gas mixing system in digester 7. The introduction of this modified mixing gas has three several positive effects on the digestion process. It stabilizes digester operation over wider daily feeding rates due to the higher ratio of methane to carbon dioxide, thus enhancing the population of methane fermenting microbes. It significantly reduces other external heating requirements and improves the heat distribution in the process through the introduction of the hot gas through the mixing system. It also significantly reduces the water content in the digester, which automatically and continually drys the sludge, eliminating the need for other drying processes and chemical polymers.

The cold water exiting the misting chamber in line 35 at a temperature on the order of 2° C. to 5° C is passed through a reverse flow heat exchanger 50 to pre-cool the water supplied to the misting chamber, then returned the treatment system through line 31. This No. 4 water is normally slightly basic with a pH of around 7.8. The carbon dioxide dissolved in the water from the mixing chamber forms carbonic acid which buffers the caustic effluent from the secondary sedimentation tank 11a. This forms salts of the caustic ions, improves the operation of the disinfection processor 18, and neutralizes the final effluent delivered to output line 19.

As noted above, converting the warm raw gas to cold dry methane prior to the mixing compressor doubles the volumetric efficiency of the gas. This means that 50% of the methane from compressor 37 is available for other uses such as an absorption chiller/heater 41 and a gas driven electrical generator 52 without sacrificing digester performance or using a larger gas compressor.

Chiller/heater 41 is part of a standard direct-fired gas absorption chiller/heater closed loop refrigeration and heating system which also includes a condenser heating chamber 40, an expansion valve 47 and the evaporator cooling coils 44 in demisting chamber 34. The chiller/heater compresses the refrigerant gas to a high pressure and temperature. The condenser heating chamber releases the heat of compression and vaporization to the surroundings, and returns the high pressure gas to its liquid state. The expansion valve controls the release of the liquid through the evaporator cooling coils and back to the low pressure side of chiller/heater 41. Expansion and evaporation of the liquid in the evaporator cooling coils cools the gas in the misting chamber.

The digester heating system 54, which was previously supplied with heat from the boiler 26, is now heated with hot water from heating coils 55 in condenser heating chamber 40. All of the excess heat available at hot water heating coils 55 is routed to a process water heat exchanger 51 which heats activated secondary sludge from line 13. The heated sludge is delivered to the digester and to the aeration basins through lines 29, 32 with control valves 56, 57 in the two lines to add process heat to the aerobic system.

The invention can be utilized both in new plants and in existing ones. As can be seen by comparing FIGS. 1 and 3, when it is added to an existing system, it eliminates the need for carbon dioxide tank 16, injector 17, sludge thickener 22, polymer injector 23, pasteurization apparatus 24, and boiler 26. These elements are made redundant or unnecessary by the invention. There are two new lines 30, 31. Line 30 is used to split off a portion of the secondary effluent in line 12, feeding it to reverse flow heat exchanger, from which line 31 returns it to a point in line 12 downstream from line 30. Secondary sludge line 13 is rerouted through process water heat exchanger, following which it split into lines 29, 32 and routed to digester 7 and to the activated sludge return pump 20 and/or by-pass line 21.

In one presently preferred embodiment, all of the elements illustrated in FIG. 2, with the possible exception of reverse flow heat exchanger 50 and process water heat exchanger 51 are packaged in a single unit which is mounted on top of or beside the digester. When the two heat exchangers are not included in the unit, they are mounted as close to it as possible.

The invention has a number of important features and advantages. It provides clean, dry, cold, dense methane gas at atmospheric pressure for efficient heating, mixing and alternate energy utilization. It increases the production of methane gas by a factor more than three, and it also increases the rate of biosolid reduction in the digester by a factor of more than three. It significantly reduces the rate of deterioration, maintenance and replacement of the major equipment associated with the gas stream, and it stabilizes the digestion process by eliminating acid products from the mixing gas. It increases the efficiency of the gas used in the mixing process by heating the gas and expanding its volume. It automatically and continually drys and thickens the sludge in the digester mixing process, eliminates the need for other thickening processes, and greatly improves the environmental acceptance of the sludge by providing total pasteurization. It eliminates the need to add chemicals except as may be used in the final disinfection stage. It provides a buffering solution to the final effluent, and provides a positive environmental impact by eliminating the discharge of carbon dioxide and hydrogen sulfide to the atmosphere. It improves the rate and efficiency of the aerobic process by supplying certain amounts of process heat, and it creates all of the additional energy required to operate the system.

In sum, the invention provides a practical way to effectively and economically produce a valuable energy product from raw anaerobic digester gas at atmospheric pressure, while simultaneously stabilizing the digestive process and providing general simplification of the wastewater treatment process.

It is apparent from the foregoing that a new and improved INVENTION has been provided. While only certain presently preferred embodiments have been described in detail, as will be apparent to those familiar with the art, certain changes and modifications can be made without departing from the scope of the invention as defined by the following claims.

What is claimed is:

1. In a gas separation system: a source of raw gas containing methane and other gaseous components, and means for cooling the gas at atmospheric pressure in the presence of a liquid to a temperature at which the other gaseous components have a substantially higher solubility in the liquid than methane and are substantially all absorbed into the liquid without changing state, leaving pure, dry methane gas.

2. In an anaerobic digestion system: means for producing a raw gas containing methane and other gaseous components, and means for misting the gas with process water which has been separated from sludge in the system to cool the gas at atmospheric pressure to a temperature at which the other gaseous components have a substantially higher solubility in water than methane and are substantially all absorbed into the water without changing state, leaving dry methane gas.

3. In a gas separation: a source of raw gas containing methane and other gaseous components, and a cooling coil for cooling the gas at atmospheric pressure in the presence of a liquid to a temperature at which the other gaseous components have a substantially higher solubility in the liquid than methane and are substantially all absorbed into the liquid without changing state, leaving pure, dry methane gas.

4. The system of claim 3 wherein the cooling coil is part of a refrigeration system which also includes a chiller/heater that burns the methane gas produced from the raw gas.

5. In an anaerobic digestion system: means for producing a raw gas containing methane and other gaseous components, means for cooling the gas at atmospheric pressure in the presence of a liquid to a temperature at which the other gaseous components have a substantially higher solubility in the liquid than methane and are substantially all absorbed into the liquid without changing state, leaving pure, dry methane gas, and means for compressing and heating the methane gas and supplying the heated methane gas to a digester in the system.

6. In a process for separating methane gas from a raw gas containing methane and other gaseous components, the step of cooling the gas at atmospheric pressure in the presence of water to a temperature at which the other gaseous components have a substantially higher solubility in water than methane and are substantially all absorbed into the water without changing state, leaving pure, dry methane.

7. In a process for separating methane gas from a raw gas containing methane and other gaseous components, the step of cooling the gas at atmospheric pressure in the presence of a liquid to a temperature at which the other gaseous components have a substantially higher solubility in the liquid than methane and are substantially all absorbed into the liquid without changing state, leaving pure, dry methane.

8. In an anaerobic digestion process which produces a raw gas containing methane and other gaseous components, the step of cooling the gas at atmospheric pressure in the presence of water to a temperature no higher than about 5° C. where the other gaseous components have a substantially higher solubility in water than methane and are substantially all absorbed into the water without changing state, leaving pure, dry methane.

9. In an anaerobic digestion process which produces a raw gas containing methane and other gaseous components, the step of misting the gas with process water which has been separated from sludge in the anaerobic digestion process to cool the gas at atmospheric pressure to a temperature at which the other gaseous components have a substantially higher solubility in the liquid than methane and are substantially all absorbed into the liquid without changing state, leaving pure, dry methane.

10. In a gas separation process, the step of cooling a gas containing methane and other gaseous components in the presence of a liquid at atmospheric pressure to a temperature at which the other gaseous components have a substantially higher solubility in the liquid than methane and are substantially all absorbed into the liquid without changing state, leaving pure, dry methane, the gas being cooled by a refrigeration system which is powered by burning the methane gas.

11. In an anaerobic digestion process which produces a raw gas containing methane and other gaseous components, the steps of cooling the gas in the presence of a liquid at atmospheric pressure to a temperature at which the other gaseous components have a substantially higher solubility in the liquid than methane and are substantially all absorbed into the liquid without changing state, leaving pure, dry methane, and compressing and heating the methane gas and supplying the heated methane gas to a digester.

12. In a gas separation system: a source of raw gas containing methane, carbon dioxide and hydrogen sulfide, and means for cooling the gas at atmospheric pressure in the presence of water to a temperature no higher than about 5° C. so that the carbon dioxide and the hydrogen sulfide are almost totally absorbed into the water without changing state, leaving pure, dry methane gas.

13. In a process for separating methane gas from a raw gas containing methane, carbon dioxide and hydrogen sulfide, the step of cooling the gas in the presence of water to a temperature no higher than about 5° C. so that the carbon dioxide and the hydrogen sulfide are almost totally absorbed into the water without changing state, leaving pure, dry methane gas.

14. In a process for separating methane gas from a raw gas containing methane, carbon dioxide and hydrogen sulfide, the step of cooling the gas at atmospheric pressure in the presence of water to a temperature no higher than about 5° C. so that the carbon dioxide and the hydrogen sulfide are almost totally absorbed into the water without changing state, leaving pure, dry methane gas.

* * * * *